United States Patent
Vahala et al.

(10) Patent No.: US 10,282,064 B2
(45) Date of Patent: May 7, 2019

(54) GRAPHICAL USER INTERFACE FOR MEDICAL INSTRUMENTS

(71) Applicant: KONINKLIJKE PHILIPS N.V., Eindhoven (NL)

(72) Inventors: Erkki Tapani Vahala, Hyvinkaa (FI); Mika Petri Ylihautala, Vantaa (FI); Melanie Suzanne Kotys, Shaker Heights, OH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 942 days.

(21) Appl. No.: 14/407,831

(22) PCT Filed: May 31, 2013

(86) PCT No.: PCT/IB2013/054506
§ 371 (c)(1),
(2) Date: Dec. 12, 2014

(87) PCT Pub. No.: WO2013/190413
PCT Pub. Date: Dec. 27, 2013

(65) Prior Publication Data
US 2015/0169836 A1 Jun. 18, 2015

Related U.S. Application Data

(60) Provisional application No. 61/661,842, filed on Jun. 20, 2012.

(30) Foreign Application Priority Data

Aug. 28, 2012 (EP) .................................... 12181954

(51) Int. Cl.
G06F 19/00 (2018.01)
A61B 5/055 (2006.01)
(Continued)

(52) U.S. Cl.
CPC ............ *G06F 3/0484* (2013.01); *A61B 5/015* (2013.01); *A61B 5/055* (2013.01); *A61B 5/7435* (2013.01);
(Continued)

(58) Field of Classification Search
CPC ..... A61B 18/12; A61B 18/1815; A61B 18/20; A61B 2018/00577; A61B 2034/254;
(Continued)

(56) References Cited

U.S. PATENT DOCUMENTS 7,831,289 B2  11/2010 Riker et al.

FOREIGN PATENT DOCUMENTS

JP   2004166975 A   6/2004
JP   2009160308 A   7/2009
(Continued)

OTHER PUBLICATIONS

Qatarneh, Sharif M. et al "Evaluation of a Segmentation Procedure to Delineate Organs for use in Construction of a Radiation Therapy Planning Atlas", Medical Informatics, vol. 69, 2003, pp. 39-55.
(Continued)

*Primary Examiner* — Michael T Rozanski

(57) ABSTRACT

The invention provides for medical instrument (200, 300) comprising a medical imaging system (202, 302) for acquiring medical image data (236) from an imaging zone (204) and a treatment system (206, 322) for depositing energy into a treatment zone (208). A processor executing instructions receives (100) a selection of a reference location and one or more anatomical references. The instructions cause the processor to repeatedly: deposit energy into the subject using a treatment system; acquire medical imaging data with the medical imaging system; determine a cumulative dosage data from the medical image data; determine (112) a first registration (242) for the reference location; determine (114)
(Continued)

a second registration (244) for the one or more anatomical references; render (116) the medical image, the one or more anatomical references, and the cumulative dosage data (270) in the graphical user interface; and halt the deposition of energy into the subject if a halt command is received from the graphical user interface.

20 Claims, 8 Drawing Sheets

(51) Int. Cl.
| | |
|---|---|
| *A61B 5/00* | (2006.01) |
| *A61B 8/00* | (2006.01) |
| *A61B 5/01* | (2006.01) |
| *A61B 8/13* | (2006.01) |
| *A61N 5/10* | (2006.01) |
| *A61B 18/20* | (2006.01) |
| *A61B 18/18* | (2006.01) |
| *A61B 18/12* | (2006.01) |
| *A61N 7/00* | (2006.01) |
| *A61N 5/00* | (2006.01) |
| *A61F 7/00* | (2006.01) |
| *G06F 3/0484* | (2013.01) |
| *A61N 7/02* | (2006.01) |
| *G01R 33/48* | (2006.01) |
| *G01R 33/54* | (2006.01) |
| *A61B 34/00* | (2016.01) |
| *G16H 40/63* | (2018.01) |
| *A61B 18/00* | (2006.01) |
| *A61B 90/00* | (2016.01) |

(52) U.S. Cl.
CPC .............. *A61B 8/13* (2013.01); *A61B 8/465* (2013.01); *A61B 18/12* (2013.01); *A61B 18/1815* (2013.01); *A61B 18/20* (2013.01); *A61B 34/25* (2016.02); *A61F 7/00* (2013.01); *A61N 5/00* (2013.01); *A61N 5/1084* (2013.01); *A61N 7/00* (2013.01); *A61N 7/02* (2013.01); *G01R 33/4808* (2013.01); *G01R 33/546* (2013.01); *G06F 19/00* (2013.01); *G16H 40/63* (2018.01); *A61B 2018/00577* (2013.01); *A61B 2034/254* (2016.02); *A61B 2090/374* (2016.02); *F04C 2270/041* (2013.01); *G01R 33/4814* (2013.01)

(58) Field of Classification Search
CPC ... A61B 2090/374; A61B 34/25; A61B 5/015; A61B 5/055; A61B 5/7435; A61B 8/13; A61B 8/465; A61F 7/00; A61N 5/00; A61N 5/1084; A61N 7/00; A61N 7/02; F04C 2270/041; G01R 33/4808; G01R 33/4814; G01R 33/546; G06F 19/3406; G06F 3/0484
See application file for complete search history.

(56) References Cited

FOREIGN PATENT DOCUMENTS

| | | |
|---|---|---|
| JP | 2011182983 A | 9/2011 |
| WO | 2012049628 A1 | 4/2012 |

OTHER PUBLICATIONS

Young, Stewart et al "Automated Planning of MRI Neuro Scans", Medical Imaging, vol. 6144, 2006.

Zouridakis, George et al "Computational Tools for MRI-Guided Thermal Therapy", WSEAS Transaction on Systems WSEAS Greece, vol. 3, No. 5, Jul. 2004, pp. 2308-2312.

1000     1002

1100     1102

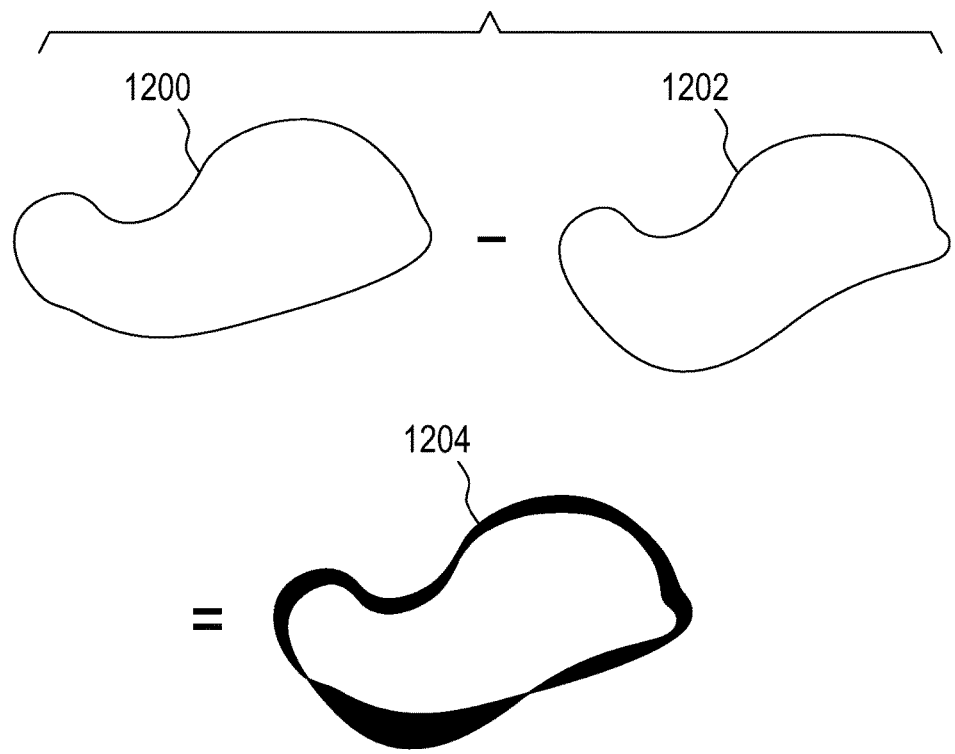

GRAPHICAL USER INTERFACE FOR MEDICAL INSTRUMENTS

CROSS-REFERENCE TO PRIOR APPLICATIONS

This application is the U.S. National Phase application under 35 U.S.C. § 371 of International Application No. PCT/IB2013/054506, filed on May 31, 2013, which claims the benefit of U.S. Provisional Patent Application No. 61/661,842, filed on Jun. 20, 2012 and European Patent Application No. 12181954.4, filed on Aug. 28, 2012. These applications are hereby incorporated by reference herein.

TECHNICAL FIELD

The invention relates to graphical user interfaces for controlling medical instruments, in particular to displaying medical images on a display for reducing the cognitive burden for stopping or pausing a treatment.

BACKGROUND OF THE INVENTION

Tissue movement, e.g., due to respiratory or peristaltic motion, creates unwanted side effects and hampers the effectiveness of a therapy device not linked to the movement. Such devices are, for example, a linear accelerator and a high intensity focused ultrasound transducer. Automated motion correction tries to remove motion related imperfections with respect to the therapy plan. Such correction can be arranged with external sensors (e.g., respiratory/ECG sensors) or imaging modalities (MRI, ultrasound, including MRI navigators and US speckle tracking).

SUMMARY OF THE INVENTION

The invention provides for a medical instrument and a computer program product in the independent claims. Embodiments are given in the dependent claims.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network. Computer executable code embodied on a computer readable medium may be transmitted using any appropriate medium, including but not limited to wireless, wireline, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage is any non-volatile computer-readable storage medium. In some embodiments computer storage may also be computer memory or vice versa.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object oriented programming language such as Java, Smalltalk, C++ or the like and conventional procedural programming languages, such as the "C" programming language or similar programming languages and compiled into machine executable instructions. In some instances the computer executable code may be in the form of a high level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It will be understood that each block or a portion of the blocks of the flowchart, illustrations, and/or block diagrams, can be implemented by computer program instructions in form of computer executable code when applicable. It is further under stood that, when not mutually exclusive, combinations of blocks in different flowcharts, illustrations, and/or block diagrams may be combined. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, gear sticks, steering wheel, pedals, wired glove, dance pad, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bistable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Medical image data is defined herein as two or three dimensional data that has been acquired using a medical imaging scanner. A medical imaging scanner is defined herein as an apparatus adapted for acquiring information about the physical structure of a patient and construct sets of two dimensional or three dimensional medical image data. Medical image data can be used to construct visualizations which are useful for diagnosis by a physician. This visualization can be performed using a computer.

Magnetic Resonance (MR) data is defined herein as being the recorded measurements of radio frequency signals emitted by atomic spins by the antenna of a Magnetic resonance apparatus during a magnetic resonance imaging scan. Magnetic resonance data is an example of medical image data. A Magnetic Resonance Imaging (MRI) image is defined herein as being the reconstructed two or three dimensional visualization of anatomic data contained within the magnetic resonance imaging data. This visualization can be performed using a computer.

Magnetic resonance data may comprise the measurements of radio frequency signals emitted by atomic spins by the antenna of a Magnetic resonance apparatus during a magnetic resonance imaging scan which contains information which may be used for magnetic resonance thermometry. Magnetic resonance thermometry functions by measuring changes in temperature sensitive parameters. Examples of parameters that may be measured during magnetic resonance thermometry are: the proton resonance frequency shift, the diffusion coefficient, or changes in the T1 and/or T2 relaxation time may be used to measure the temperature using magnetic resonance. The proton resonance frequency shift is temperature dependent, because the magnetic field that individual protons, hydrogen atoms, experience depends upon the surrounding molecular structure. An increase in temperature decreases molecular screening due to the temperature affecting the hydrogen bonds. This leads to a temperature dependence of the proton resonance frequency.

The proton density depends linearly on the equilibrium magnetization. It is therefore possible to determine temperature changes using proton density weighted images.

The relaxation times T1, T2, and T2-star (sometimes written as T2*) are also temperature dependent. The reconstruction of T1, T2, and T2-star weighted images can therefore be used to construct thermal or temperature maps.

The temperature also affects the Brownian motion of molecules in an aqueous solution. Therefore pulse sequences which are able to measure diffusion coefficients such as a pulsed diffusion gradient spin echo may be used to measure temperature.

One of the most useful methods of measuring temperature using magnetic resonance is by measuring the proton resonance frequency (PRF) shift of water protons. The resonance frequency of the protons is temperature dependent. As the temperature changes in a voxel the frequency shift will cause the measured phase of the water protons to change. The temperature change between two phase images can therefore be determined. This method of determining temperature has the advantage that it is relatively fast in comparison to the other methods. The PRF method is discussed in greater detail than other methods herein. However, the methods and techniques discussed herein are also applicable to the other methods of performing thermometry with magnetic resonance imaging.

Spectroscopic magnetic resonance data is defined herein as being the recorded measurements of radio frequency signals emitted by atomic spins by the antenna of a Magnetic resonance apparatus during a magnetic resonance imaging scan which contains information which is descriptive of multiple resonance peaks.

The spectroscopic magnetic resonance data may for instance be used to perform a proton spectroscopic (PS) imaging based temperature mapping method which can produce temperature maps on absolute scale. This absolute scale temperature map may therefore be used to perform a temperature calibration. This method relies on the physical principles of water proton resonance shift temperature dependence as the proton resonance frequency method, but the acquisition method is different: the frequency shift is calculated from the magnetic resonance spectra. The shift is calculated from the position difference of the water and a reference proton peak. Protons in lipids may for example be used as reference, as their resonance frequency is known to be almost independent of temperature, while the water proton peak has linear dependence on temperature. This can be done in the voxels, where both tissue types are present. If water and lipids do not exist in the same voxel, one may try to use some other tissue type than lipids as reference. If not successful, there may be some voxels where the reference peaks, and therefore the temperature data, are not available. Interpolation and/or temperature filtering may be used to help these situations, since body temperature is normally not expected to change rapidly spatially with the highly localized temperature rise typically caused by thermal therapy being an obvious exception. The utilization of reference peaks makes the method relatively independent of field drifts or inter-scan motion. Because the scanning takes a time of at least on the order of one minute with current methods, the PS method is susceptible to intra-scan motion or temperature change during scanning. In a case where temperature is constant or temperature variation is small both in time and space, the method is able to produce useful information. For example, with the Magnetic Resonance Guided High Intensity Focused Ultrasound (MR-HIFU), the PS method can be used to provide the actual body temperature distribution before start of MR-HIFU or other temperature treatment as opposed to using a spatially homogeneous starting temperature taken as the body core temperature measured with a thermometer probe. Alternatively, the PS method can be used as a sanity check for the cumulative temperature between heat treatments outside the treatment area.

An 'ultrasound window' as used herein encompasses a window which is effectively transparent to ultrasonic waves or energy. Typically a thin film or membrane is used as an ultrasound window. The ultrasound window may for example be made of a thin membrane of BoPET (Biaxially-oriented polyethylene terephthalate).

In one aspect the invention provides for a medical instrument comprising a medical imaging system for acquiring medical image data from an imaging zone. The medical instrument further comprises a treatment system for depositing energy into a treatment zone. The treatment zone is within the imaging zone. The treatment system is operable for depositing energy into a subject. The treatment system may deposit energy into the treatment zone in a variety of ways. For instance the treatment system could deposit energy using radio-frequency, microwave, thermal or radiation to deposit energy into the treatment zone. The medical instrument further comprises a display for displaying a graphical user interface to an operator. The graphical user interface is operable for receiving a halt command. A halt command as used herein encompasses a command which causes the treatment system to cease and/or to delay the depositing of energy into the treatment zone. The medical instrument further comprises a processor for controlling the medical instrument. The medical instrument further comprises a storage for storing machine-executable instructions for execution by the processor. Execution of the instructions causes the processor to receive a selection of a reference location. The reference location may be a specific point, region or volume of the subject. In some cases the reference location may be the treatment zone.

Execution of the instructions further causes the processor to receive a selection of one or more anatomical references. An anatomical reference as used herein may encompass a region of the anatomy of a subject that is identified by the anatomical reference. Execution of the instructions further causes the processor to repeatedly control the treatment system to deposit energy into the subject in accordance with a treatment plan. The treatment plan may be entered into the medical instrument by an operator or the treatment plan may be pre-prepared. The treatment plan either contains instructions for operating the treatment system or other details which may be used to generate control commands for the treatment system. Execution of the instructions further causes the processor to repeatedly control the medical imaging system to acquire the medical image data. Execution of the instructions further causes the processor to repeatedly reconstruct a medical image using the medical image data. Execution of the instructions further cause the processor to determine cumulative dose data at least partially from controlling the treatment system to deposit energy into the subject. The data which is used for generating or determining the cumulative dosage data may for instance come from the treatment plan or it may also come in terms of feedback from control parameters, images, or sensors that are part of the treatment system. The cumulative dosage data is registered to the medical image.

Execution of the instructions further causes the processor to repeatedly determine a first registration which registers the reference location to the medical image. The first registration may be a translation or mapping which is used to position the location of the medical image. Execution of the instructions further causes the processor to repeatedly determine a second registration which registers the one or more anatomical references to the medical image. That is to say the second registration may be used to indicate the position of the anatomical references in the medical image.

In another embodiment execution of the instructions further cause the processor to repeatedly render the medical image in the graphical user interface using the first registration to place the reference location in a predetermined position in the graphical user interface. The medical image is displayed or a portion of the medical image is displayed on the graphical user interface. The first registration is used to translate or transform the medical image such that the reference location is in a known or predetermined location on the graphical user interface. For instance, if the subject moves, the reference location will however be always displayed on the same position in the graphical user interface.

In another embodiment execution of the instructions further causes the processor to render a representation of the one or more anatomical references in the graphical user interface using the second registration. For instance, an operator or physician may not recognize the location of an anatomical structure using just the medical image. Execution of the instructions further causes the processor to repeatedly render a representation of the one or more anatomical references in the graphical user interface using the second registration. Execution of the instructions further causes the processor to render the cumulative dose data in the graphical user interface. The cumulative dosage data is superimposed on the medical image. Since the cumulative dosage data is registered to the medical image the cumulative dosage data is displayed in a location over the medical image so that the physician or operator knows what the cumulative dose is. Execution of the instructions further causes the processor to control the medical imaging system to halt the deposition of energy into the subject if the halt command is received from the graphical user interface.

This embodiment may be beneficial because providing the data as described above rendered on a graphical user interface and providing a graphical user interface that is operable for receiving a halt command, the cognitive burden of a user manually stopping or pausing the operation of a treatment system is greatly reduced.

In another embodiment execution of the instructions further causes the processor to receive display plane position data and orientation data from the user interface. Execution of the instructions further causes the processor to interpolate the medical image data to display multi-planar-reconstructed slices in the graphical user interface using the display position and orientation data.

This embodiment may be beneficial because the use of the interpolated image data determined by the displayed plane position may provide a view to the user which further reduces the cognitive burden of deciding or operating the user interface to halt the sonication or heating.

In another embodiment execution of the instructions further causes the processor to display a template display tool on the graphical user interface. The template display tool is operable for selecting at least one template display plane position. Execution of the instructions further causes the processor to render the medical image in accordance with the at least one template display plane position, using the target zones and/or anatomical references as template parameters for automatically positioning the display plane positions.

In another embodiment, the template display planes are linear accelerator beam views, that is, planes that are centered on the target zone and oriented at fixed gantry angles to cover the target from various directions, and the template parameter is the target zone registration. As a result, if the target zone moves and planes are re-rendered, the beam views are seen centered on the target zone. This embodiment may be beneficial because moving the beam views with the target zone reduces the cognitive burden as the user is not forced to mentally stabilize the flickering images as the target moves in and out of the display planes.

In another embodiment the template plane is operable for displaying a distance between the reference location and the at least one of the one or more anatomical references. This embodiment may be beneficial because providing a number may further make the cognitive burden of operating the graphical user interface reduced.

In another embodiment the template display plane is operable for displaying the distance between the reference location and the at least one of the one or more anatomical references. In some embodiments this may be the shortest distance between a worst affected portion of an anatomical structure regardless of the respective position of the viewing plane.

In another embodiment execution of the instructions further causes the processor to determine a display plane containing the reference location and the at least one of the one or more anatomical references. The medical image is at least partially rendered along the display plane.

In another embodiment execution of the instructions further cause the processor to render the one or more anatomical reference objects such that the position of the one or more anatomical references is displayed for multiple time periods. Implementation of this embodiment may in some cases cause an image of an anatomical reference to be smeared or shown at repeated times. The anatomical reference can also be shown with tracking history and an optional time filtering of the images. The object is shown as smeared and cumulative overlapping of tracking data.

In another embodiment the memory further contains a four-dimensional image set descriptive of the subject. This may for instance be pre-acquired medical image data obtained at an earlier time period or during an examination for planning the treatment of the subject. The one or more anatomical references and the reference location are registered to the four-dimensional image set. Execution of the instructions further causes the processor to determine position data using the medical image data. The position data is descriptive of a cyclical motion of the subject. Position data as used herein encompasses any data which may be used to determine the cyclical nature of the motion of the subject. For instance in magnetic resonance imaging the position data may for instance by a navigator or a small region of the subject is imaged and used to infer the overall motion or internal motion of the subject. For instance the position of the diaphragm may be used to determine the phase of the subject's breathing. Similar measurements may also be used for determining the position of the subject's heart.

Execution of the instructions further causes the processor to select a three-dimensional subset of the four-dimensional image set using the position data. In this step the position data is used to determine where in the cyclical motion of the subject the subject is presently and select a three-dimensional subset which corresponds to it. Execution of the instructions further causes the processor to render the three-dimensional subset and the one or more anatomical references as a single image in the graphical user interface. The reference location is located at a second predetermined location in the graphical user interface. This may be beneficial in some cases when it is not possible to acquire the medical image data rapidly enough to always show a clear image of the subject. For instance the medical image data may be used to simply determine where the subject is in the cyclical motion and then select the appropriate data.

In another embodiment execution of the instructions further causes the processor to repeatedly replace at least a portion of the four-dimensional image set with the medical image. During the course of operating the system the medical imaging system may acquire medical image data which is sufficiently high enough resolution such that portions of the four-dimensional image set may be replaced.

In another embodiment execution of the instructions further causes the processor to render the one or more anatomical references such that the position of the one or more anatomical references is displayed for at least an entire period of the cyclical motion of the subject. This may be extremely beneficial because as the energy is deposited into the treatment zone portions of the subject may move cyclically. By illustrating the anatomical references for an entire period the operator may better gauge if the region indicated by the anatomical reference will move or interfere with the treatment zone.

In another embodiment execution of the instructions further causes the processor to detect a failure descriptive of a failure to determine the second registration and/or the failure to determine the cumulative dose data. Execution of the instructions further causes the processor to render a failure notification in the graphical user interface if the failure is detected. For instance the user may be notified about the failures in the motion correction or therapy effect determination problems. This may be when the automated organ and/or tissue tracking fails to locate or determine with sufficient accuracy the location and/or shape of the tracked object. This may also occur when the algorithm calculating the effect is unable to produce a result. In some embodiments the notification may be a warning glyph or icon displayed in the graphical user interface.

In another embodiment execution of the instructions further cause the processor to detect a tracking failure descriptive of a failure to register the cumulative dose data and/or register the one or more anatomical references to the medical image. Execution of the instructions further causes the processor to render a modified cumulative dose data and/or representation in the graphical user interface if the tracking failure is detected. For instance the user may be notified about the failure in motion correction with the one or more anatomical references or the cumulative dose data. The one or more of these objects may be shown as frozen, that is that they are not moving, and with a different line style. For instance they may have dotted lines and/or different colors to distinguish them from objects that are being properly tracked.

In another embodiment the treatment system is a high-intensity focused ultrasound system.

In another embodiment the treatment system is a radio-frequency heating system.

In another embodiment the treatment system is a microwave ablation system.

In another embodiment the treatment system is a hyperthermia therapy system.

In another embodiment the treatment system is a laser ablation system.

In another embodiment the treatment system is an infrared ablation system.

In another embodiment the treatment system is a tissue heating system.

In another embodiment the treatment system is a radiation therapy system.

In another embodiment the treatment system is a gamma knife.

In another embodiment the treatment system is a charged particle treatment system. In this embodiment charged particles are accelerated and targeted at the treatment zone.

In another embodiment the treatment system is a radiotherapy treatment system.

In another embodiment the medical imaging system is a computer tomography system.

In another embodiment the medical imaging system is a magnetic resonance imaging system.

In another embodiment the medical imaging system is a diagnostic ultrasound imaging system.

In another embodiment the medical imaging system is a magnetic resonance imaging system. The treatment system is a high-intensity focused ultrasound system. The magnetic resonance imaging system is further operable for acquiring thermal magnetic resonance data. Execution of the instructions further causes the processor to control the magnetic resonance imaging system to acquire the thermal magnetic resonance imaging data. Execution of the instructions further causes the processor to determine a thermal dose map from the thermal magnetic resonance data. The cumulative dose data is constructed from the thermal dose map.

In another embodiment execution of the instructions further cause the processor to register treatment status data to the medical image. Execution of the instructions further causes the processor to render the treatment status data in the graphical user interface. The treatment status data is superimposed on the medical image. The treatment status data may comprise any one of the following: a predictive model of treatment zone motion, position of a multi-leaf collimator leaves from the beam's eye view superimposed on the medical image, isodose curves from a treatment plan, a contour of the target within the subject, critical anatomical structures, and combinations thereof.

In another aspect the invention provides for a computer program product comprising machine-executable instructions for execution by a processor controlling the medical instrument. The medical instrument comprises a medical imaging system for acquiring medical image data from an imaging zone. The medical instrument further comprises a treatment system for depositing energy into a treatment zone. The treatment zone is within the imaging zone. The treatment system is operable for depositing energy into a subject. The medical instrument further comprises a display for displaying the graphical user interface to an operator. The graphical user interface is operable for receiving a halt command. Execution of the instructions causes the processor to receive a selection of a reference location. Execution of the instructions further causes the processor to receive a selection of one or more anatomical references.

Execution of the instructions further causes the processor to repeatedly control the treatment system to deposit energy into the subject in accordance with a treatment plan. Execution of the instructions further causes the processor to repeatedly control the medical imaging system to acquire the medical image data. Execution of the instructions further causes the processor to repeatedly reconstruct a medical image using the medical image data. Execution of the instructions further cause the processor to repeatedly determine a cumulative dosage data at least partially from controlling the treatment system to deposit energy into the subject, wherein the cumulative dosage data is registered to the medical image. Execution of the instructions further causes the processor to repeatedly determine a first registration which registers the reference location of a medical image.

Execution of the instructions further causes the processor to repeatedly determine a second registration which registers the one or more anatomical references to the medical image. Execution of the instructions further cause the processor to repeatedly render the medical image in the graphical user interface using the first registration to place the reference location in a predetermined position in the graphical user interface. Execution of the instructions further cause the processor to repeatedly render a representation of the one or more anatomical references in the graphical user interface using the second registration. Execution of the instructions further causes the processor to repeatedly render the cumulative dosage data in the graphical user interface. The cumulative dosage data is superimposed on the medical image. Execution of the instructions further cause the processor to repeatedly control the medical imaging system to halt the deposition of energy into the subject if the halt command is received from the graphical user interface.

It is understood that one or more of the aforementioned embodiments of the invention may be combined as long as the combined embodiments are not mutually exclusive.

BRIEF DESCRIPTION OF THE DRAWINGS

In the following preferred embodiments of the invention will be described, by way of example only, and with reference to the drawings in which:

FIG. 12 illustrates a method of displaying an anatomical reference to illustrate its movement over time.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
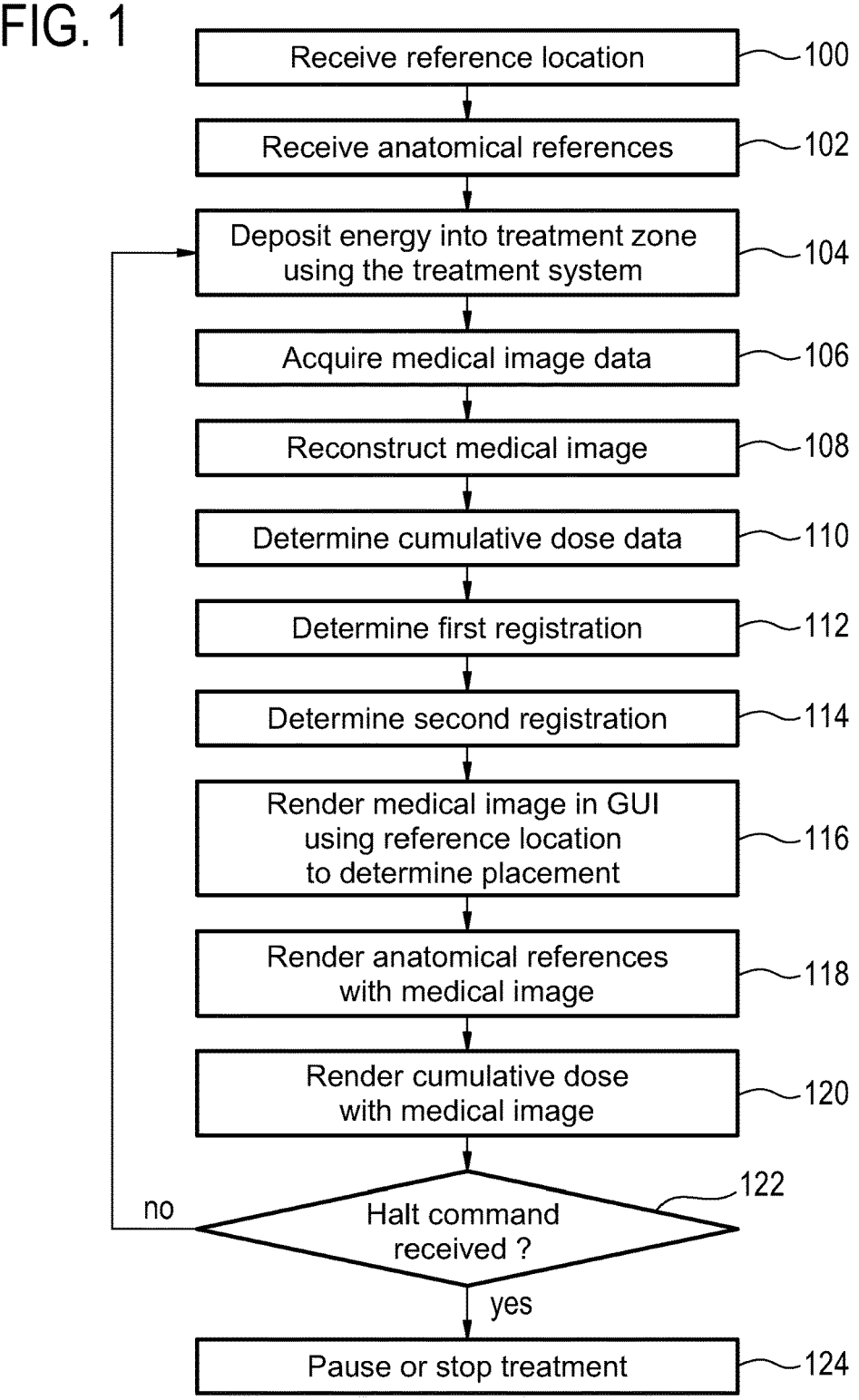
FIG. 1 shows a flow diagram which illustrates a method according to an embodiment of the invention.

FIG. 1 shows a flow diagram which illustrates a method according to an embodiment of the invention. First in step 100 a reference location is received. This may for instance be received from a graphical user interface or it may be data which is received from a memory or from another computer system. Likewise in step 102, anatomical references are received. The anatomical references may also be received in the same way that the reference location was received. In some embodiments the reference location and the anatomical references will be received within part of a treatment plan. Next in step 104 energy is deposited into a treatment zone using the treatment system. Next in step 106 medical image data is acquired. Steps 104 and 106 may be performed concurrently or performed in any order with respect to each other.

Next in step 108 a medical image is reconstructed from the medical image data. Next in step 110 cumulative dose data is determined. This may for instance be constructed using data from a treatment plan, feedback from the treatment system or from measurements made using the medical image data. Next in step 112 a first registration is determined using the medical image. Next in step 114 a second registration is determined using the medical image. The first registration determines the location of a reference location within the medical image. The second registration determines the location of one or more anatomical references within the medical image. Next in step 116 a medical image is rendered to the graphical user interface using the reference location to determine placement of the medical image. Next in step 118 an anatomical reference is rendered along, on top of or beneath or superimposed on the medical image in the graphical user interface. Next in step 120 the cumulative dose data is rendered along with the medical image. If a halt command 122 has been received during any portion of this process the treatment system halts the deposition of energy into the treatment zone. This may for instance be a pause in the deposition of energy or it may be an abort of cancellation of the treatment. If the halt command is received, then the method proceeds to step 124 which represents a pause or a stop of treatment. If the halt command has not been received then the method returns back to step 104 and the process is repeated until a halt command is received or until the entire treatment is finished.

Figure 2:
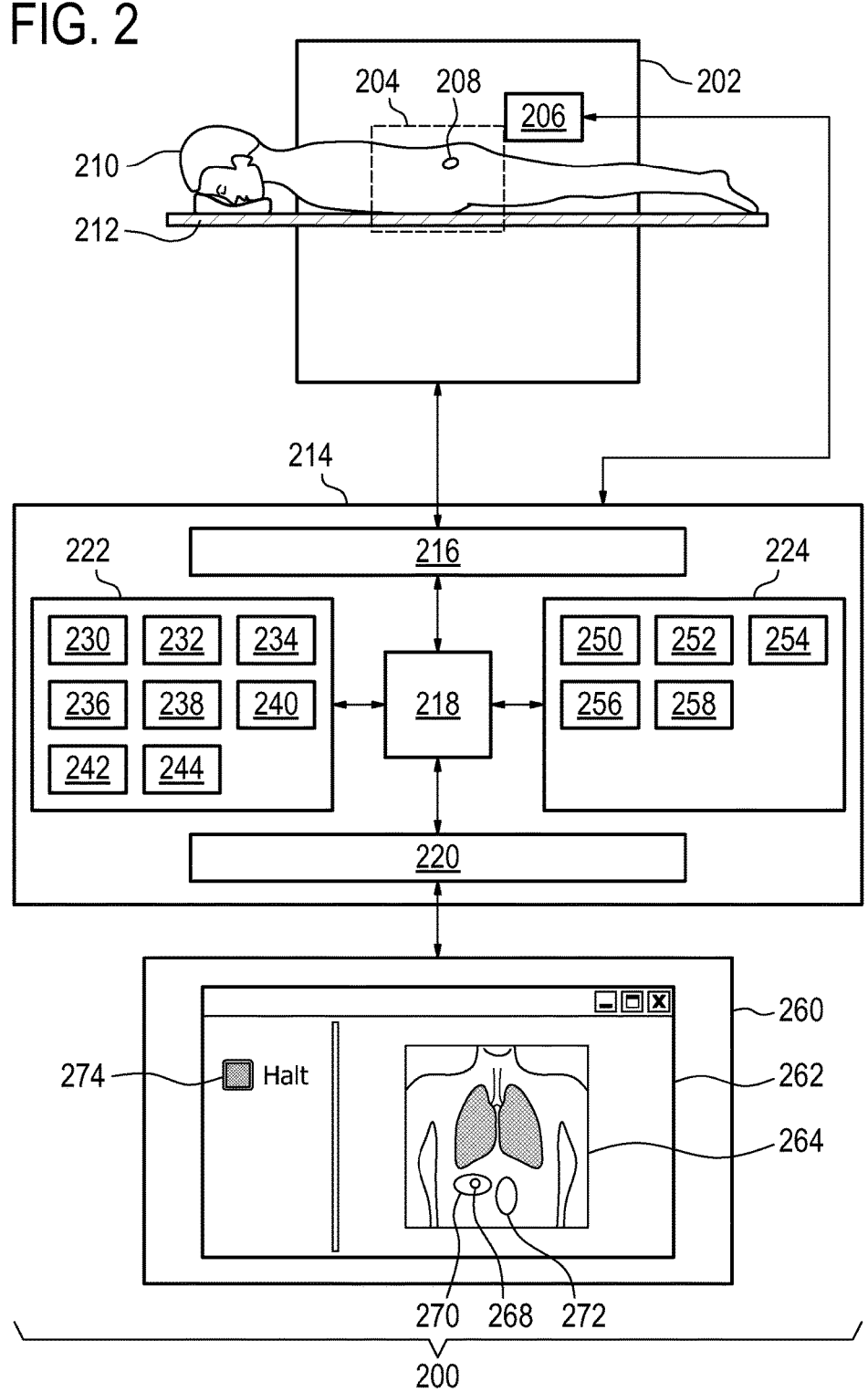
FIG. 2 illustrates a medical instrument according to an embodiment of the invention.

FIG. 2 illustrates a medical instrument 200 according to an embodiment of the invention. The medical instrument 200 comprises a medical imaging system 202 which has an imaging zone. The medical imaging system 202 is intended to be representative and may represent, but is not limited to: a computer tomography system, a magnetic resonance imaging system, and a diagnostic ultrasound imaging system.

The medical instrument 200 further comprises a treatment system 206 for directing energy into a treatment zone 208. The treatment zone 208 is within the imaging zone 204. A subject 210 can be seen reposing on a subject support 212. The subject 210 is partially within the imaging zone 204 and the treatment zone 208 is within the subject 210. This enables the treatment system 206 to direct energy into the portion of the subject 210 indicated by the treatment zone 208. The treatment system 206 is intended to be representative and may represent, but is not limited to: a high-intensity focused ultrasound system, a radio-frequency heating system, a microwave ablation system, a hyperthermia therapy system, a laser ablation system, an infrared ablation system, a tissue heating system, a radiation therapy system, a gamma knife, a charged particle therapy system, and a radiotherapy treatment system.

The medical imaging system 202 and the treatment system 206 are seen as being connected to a hardware interface 216 of a computer system 214. The computer system 214 further comprises a processor 218 which is connected to the hardware interface 216. The processor 218 is further connected to a user interface 220, computer storage 222, and computer memory 224. The hardware interface 216 enables the processor 218 to control the operation and function of the medical instrument 200. The computer storage 222 is shown as containing a treatment plan 230. The treatment plan 230 either contains instructions which may be used for controlling the treatment system 206 or it contains information which is useful for generating commands for controlling the treatment system 206. The computer storage 222 is further shown as containing a selection of the reference location 232. The computer storage 222 is further shown as containing the selection of anatomical references 234. The computer storage 222 is further shown as containing medical image data 236 acquired with the medical imaging system 202. The computer storage 222 is further shown as containing a medical image 238 which is reconstructed from the medical image data 236. The computer storage 222 is further shown as containing cumulative dosage data 240 that was calculated using the treatment plan 230, the medical image 238, and/or data received by the processor 218 from the treatment system 208. The computer storage 222 is further shown as containing a first registration 242 which registers the reference location 232 to the medical image 238. The computer storage 222 is further shown as containing a second registration which registers the locations of the anatomical references 234 to the medical image 238.

The computer memory 224 is shown as containing a control module 250. The control module 250 contains computer-executable code which enables the processor 218 to control the operation and function of the entire medical instrument 200. For instance the control module 250 may be used to generate commands for directly controlling the medical imaging system 202 and the treatment system 206. The computer memory 224 is further shown as containing an image reconstruction module 252. The image reconstruction module 252 contains computer-executable code which enables the processor 218 to generate the medical image 238 from the medical image data 236. The computer memory 224 is further shown as containing an image registration module 254. The image registration module 254 contains computer-executable code which enables the processor 218 to generate the first registration 242 and the second registration 244 from the medical image 238.

The computer storage 224 further contains a dosage calculation module 256. The dosage calculation module 256 contains computer-executable code which enables the processor 218 to calculate the cumulative dosage data 240. The computer memory 224 further contains a graphical user interface module 258. The graphical user interface module 258 contains computer-executable code which enables the processor 218 to generate and display a graphical user interface 262 on a display 260.

The user interface 220 is shown as being connected to a display 260. The display 260 is rendering the graphical user interface 262. In the graphical user interface 262 is a rendering of a medical image 264. On the medical image 264 the reference location 268 may be shown. In some embodiments the reference location 268 is also the location of the treatment zone. A cumulative dose rendering 270 which is a rendering of the cumulative dosage data 240 is also shown as being superimposed on the medical image 264. Adjacent to the reference location 268 is an oval 272 which represents an anatomical reference 272. In another portion of the graphical user interface 262 is a halt button 274 which enables an operator or physician to halt the operation temporarily or to halt an entire treatment by stopping the treatment system 206.

Figure 3:
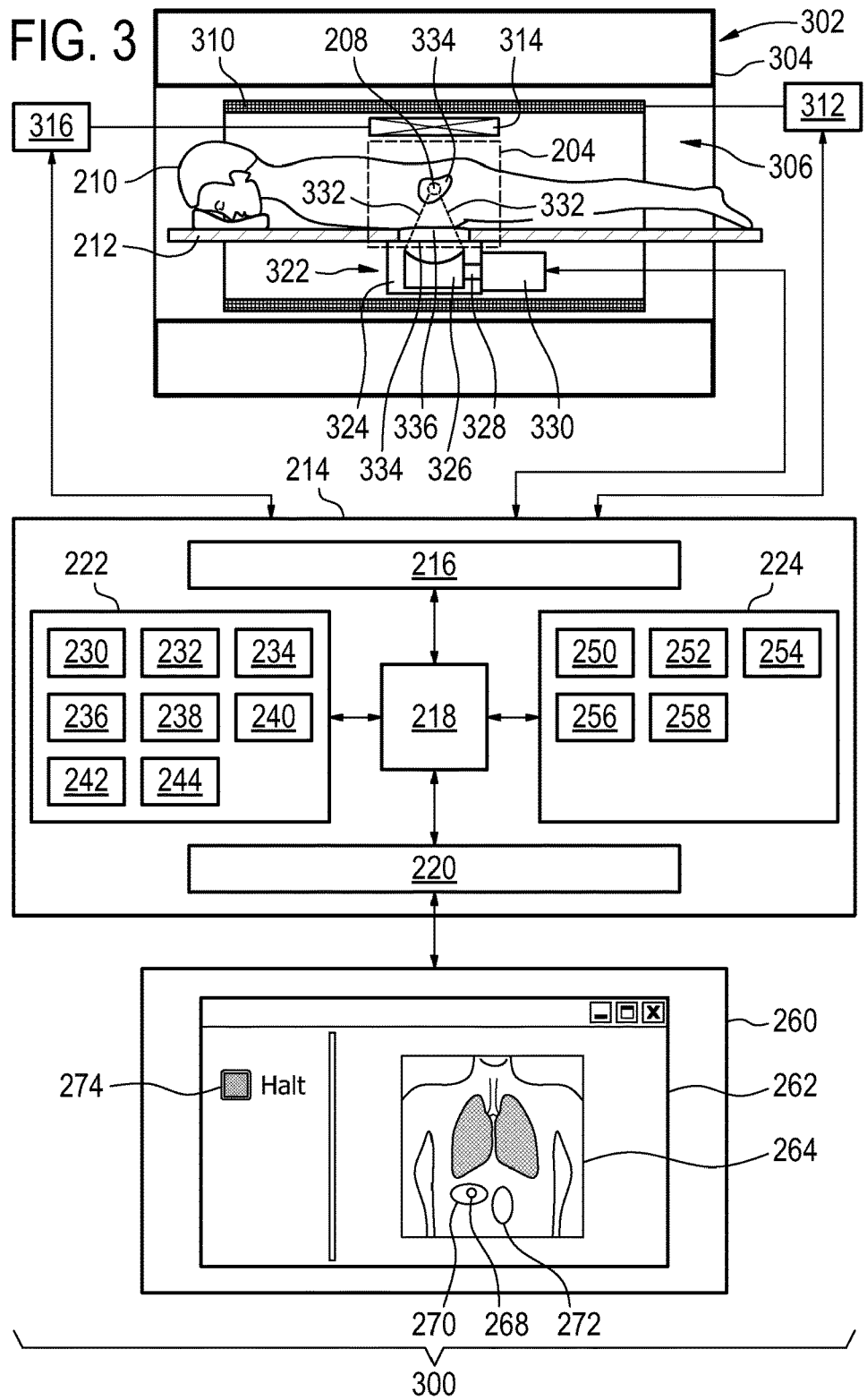
FIG. 3 illustrates a medical instrument according to a further embodiment of the invention.

FIG. 3 illustrates a medical apparatus 300 according to an embodiment of the invention. The medical apparatus 300 comprises a magnetic resonance imaging system 302 which is the medical imaging system. The magnetic resonance imaging system 302 is shown as comprising a magnet 304. The magnet 304 is a cylindrical type superconducting magnet with a bore 306 through the center of it. The magnet 304 has a liquid helium cooled cryostat with superconducting coils. It is also possible to use permanent or resistive magnets. The use of different types of magnets is also possible for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. Within the bore of the cylindrical magnet there is an imaging zone 308 where the magnetic field is strong and uniform enough to perform magnetic resonance imaging.

Also within the bore of the magnet is a magnetic field gradient coil 310 which is used for acquisition of magnetic resonance data to spatially encode magnetic spins within an imaging zone of the magnet. The magnetic field gradient coil 310 is connected to a magnetic field gradient coil power supply 312. The magnetic field gradient coil is representative. Typically magnetic field gradient coils contain three separate sets of coils for spatially encoding in three orthogonal spatial directions. A magnetic field gradient power supply 312 supplies current to the magnetic field gradient coils. The current supplied to the magnetic field coils is controlled as a function of time and may be ramped and/or pulsed.

Adjacent the imaging zone 308 is a radio-frequency coil 314. The radio-frequency coil 314 is connected to a radio-frequency transceiver 316. Also within the bore of the magnet 304 is a subject 210 that is reposing on a subject support 212 and is partially within the imaging zone 308.

Adjacent to the imaging zone 308 is a radio-frequency coil 314 for manipulating the orientations of magnetic spins within the imaging zone 308 and for receiving radio transmissions from spins also within the imaging zone 308. The radio-frequency coil 314 may contain multiple coil elements. The radio-frequency coil 314 may also be referred to as a channel or an antenna. The radio-frequency coil is connected to a radio frequency transceiver 316. The radio-frequency coil 314 and radio frequency transceiver 316 may be replaced by separate transmit and receive coils and a separate transmitter and receiver. It is understood that the radio-frequency coil 314 and the radio-frequency transceiver 316 are representative. The radio-frequency coil 314 is intended to also represent a dedicated transmit antenna and a dedicated receive antenna. Likewise the transceiver 316 may also represent a separate transmitter and a separate receiver.

The medical apparatus 300 further comprises a high-intensity focused ultrasound system as the treatment system. The high-intensity focused ultrasound system comprises a fluid-filled chamber 324. Within the fluid-filled chamber 324 is an ultrasound transducer 326. Although it is not shown in this Fig. the ultrasound transducer 326 may comprise multiple ultrasound transducer elements each capable of generating an individual beam of ultrasound. This may be used to steer the location of the sonication point 208 or treatment zone electronically by controlling the phase and/or amplitude of alternating electrical current supplied to each of the ultrasound transducer elements. The sonication point 208 is operable to be controlled to sonicate the target zone 334.

The ultrasound transducer 326 is connected to a mechanism 328 which allows the ultrasound transducer 326 to be repositioned mechanically. The mechanism 328 is connected to a mechanical actuator 330 which is adapted for actuating the mechanism 328. The mechanical actuator 330 also represents a power supply for supplying electrical power to the ultrasound transducer 326. In some embodiments the power supply may control the phase and/or amplitude of electrical power to individual ultrasound transducer elements. In some embodiments the mechanical actuator/power supply 330 is located outside of the bore 326 of the magnet 324.

The ultrasound transducer 326 generates ultrasound which is shown as following the path 332. The ultrasound 332 goes through the fluid-filled chamber 324 and through an ultrasound window 334. In this embodiment the ultrasound then passes through a gel pad 336. The gel pad is not necessarily present in all embodiments but in this embodiment there is a recess in the subject support 212 for receiving a gel pad 336. The gel pad 336 helps couple ultrasonic power between the transducer 326 and the subject 210. After passing through the gel pad 336 the ultrasound 332 passes through the subject 210 and is focused to a sonication point 208. The sonication point 208 is being focused within a target zone 334. The sonication point 208 may be moved through a combination of mechanically positioning the ultrasonic transducer 326 and electronically steering the position of the sonication point 208 to treat the entire target zone 334.

The magnetic field gradient coil power supply 312, the radio-frequency transceiver 316, and the high-intensity focused ultrasound system 322 are connected to a hardware interface 324 of a computer system 322. The computer system 214 and the contents of its storage 222 and memory 224 are equivalent to that as shown in FIG. 2.

Figure 4:
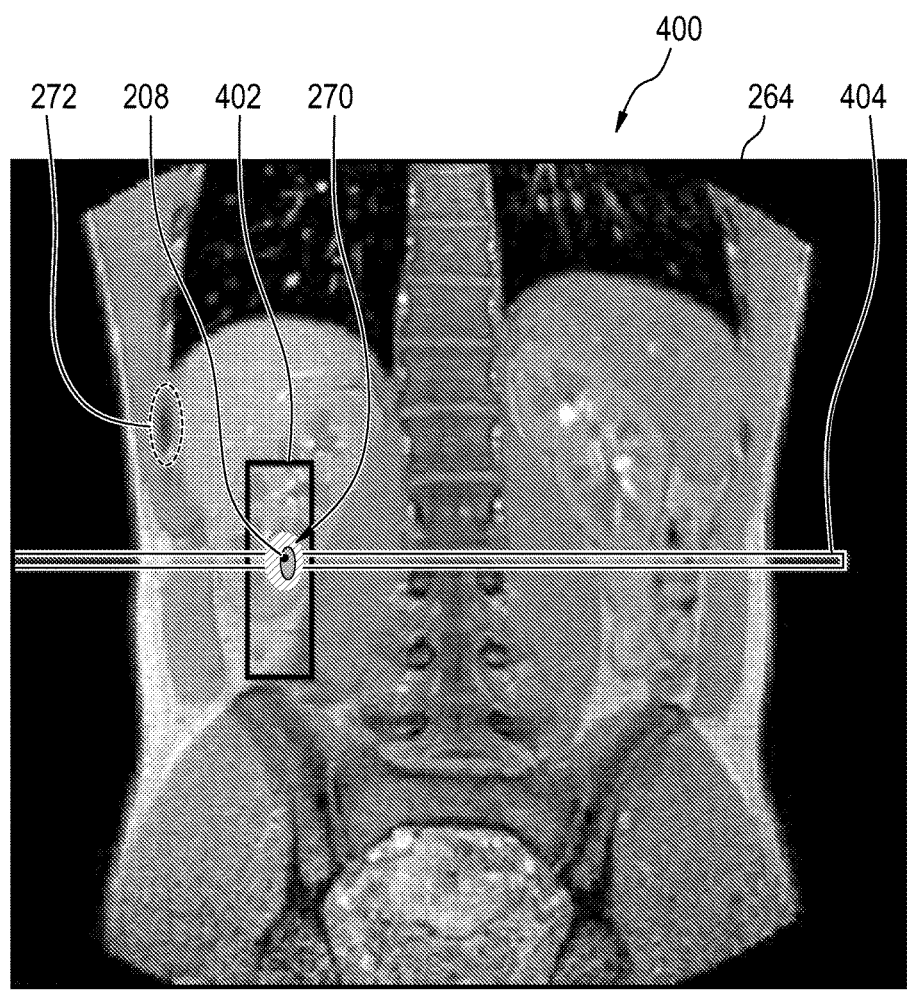
FIG. 4 shows a display plane which may be embedded in a graphical user interface.

FIG. 4 shows a display plane 400 which may be embedded in a graphical user interface. The display plane 400 contains a medical image 264. Also shown the Fig. is a treatment zone 208 which is also the reference location. There is a cumulative dosage rendering 270 superimposed. Also in the Fig. are several anatomical references 272 which are shown in the Fig. A navigator box 402 and a real-time acquisition place 404 are also shown in this figure.

Figure 5:
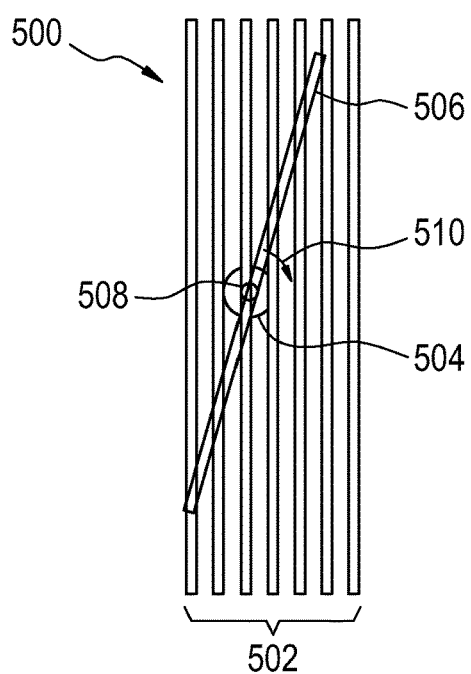
FIG. 5 illustrates a display plane modification tool which may be incorporated into a graphical user interface according to an embodiment of the invention.

FIG. 5 illustrates a display plane modification tool 500 which may be incorporated into a graphical user interface according to an embodiment of the invention. Shown are a group of seven current imaging planes 502. The target 504 is illustrated by a partial circle. The plane labeled 506 indicates the position of a modified imaging plane. The imaging plane 506 has a center 508 which may be moved. The plane 506 also has a pivot handle 510 which allows the plane 506 to rotate around the pivot 508.

Figure 6:
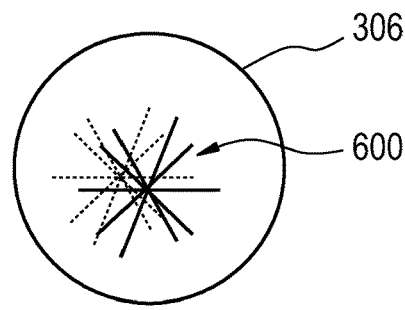
FIG. 6 illustrates templates which may be selected using the graphical user interface.

FIG. 6 illustrates templates which may be selected using the graphical user interface. In FIG. 6 the circle 306 represents the bore of a magnetic resonance imaging system. The lines marked 600 indicate five planes which may be defined relative to for example a magnetic resonance imaging LINAC beam which may be viewed at five fixed angles. The dimmed plane lines depict the absolute position of the planes relative to the bore at time t1. The solid plane lines depict their absolute position relative to the bore at time t2. At both timestamps the planes were centered on the moving target zone. The translation arrow indicates in-plane target zone movement. Selecting these planes may save the operator time in defining viewing planes and reduces target zone movement induced flicker in regularly re-rendered images.

Figure 7:
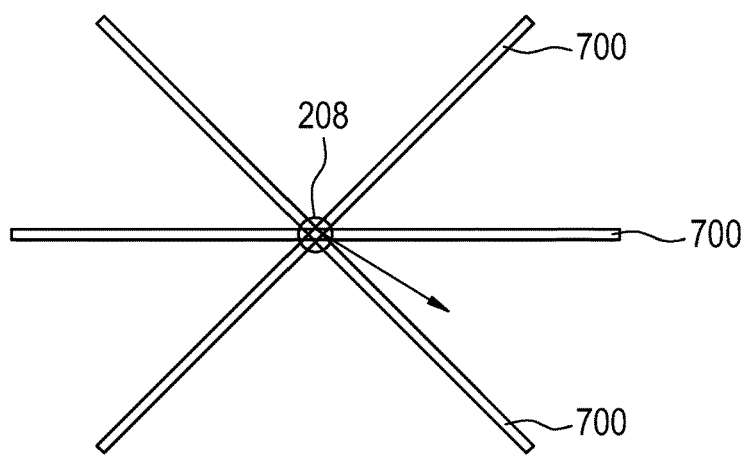
FIG. 7 illustrates a variety of imaging planes which may have their position defined relative to the reference point.

FIG. 7 illustrates a variety of imaging planes 700 which may have their position defined relative to the reference point 208. As the reference point moves the definition of the location of the planes also is moved automatically.

Figure 8:
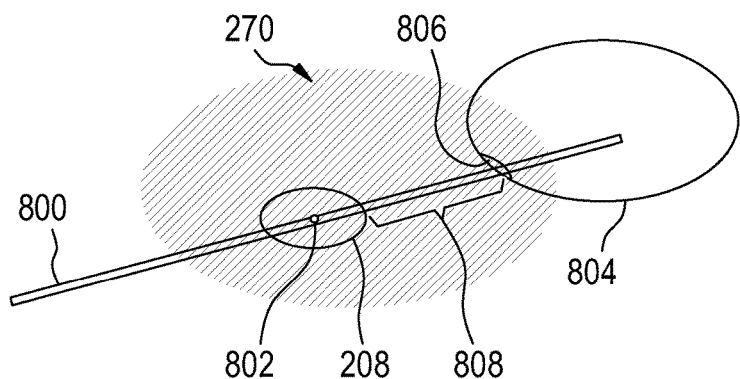
FIG. 8 illustrates the selection of a viewing plane.

FIG. 8 illustrates the selection of a viewing plane. In FIG. 8 there is a viewing plane 800. The viewing plane is positioned such that it passes through the treatment zone 208. The center of the plane 802 is located at the center of the treatment zone 208. Superimposed around this is a rendering of the cumulative dose data 270. The location of an organ at risk 804 is shown as being partially within the area treated 270. The region of the organ 804 closest to the treatment zone 208 is indicated by the region 806. This is a critical region of the organ 806. It can be seen that the plane 800 shows the distance 808 between the treatment zone 208 and the region of the organ at risk 806. The medical image data along the plane 800 reduce the cognitive burden of someone operating the graphical user interface.

Figure 9:
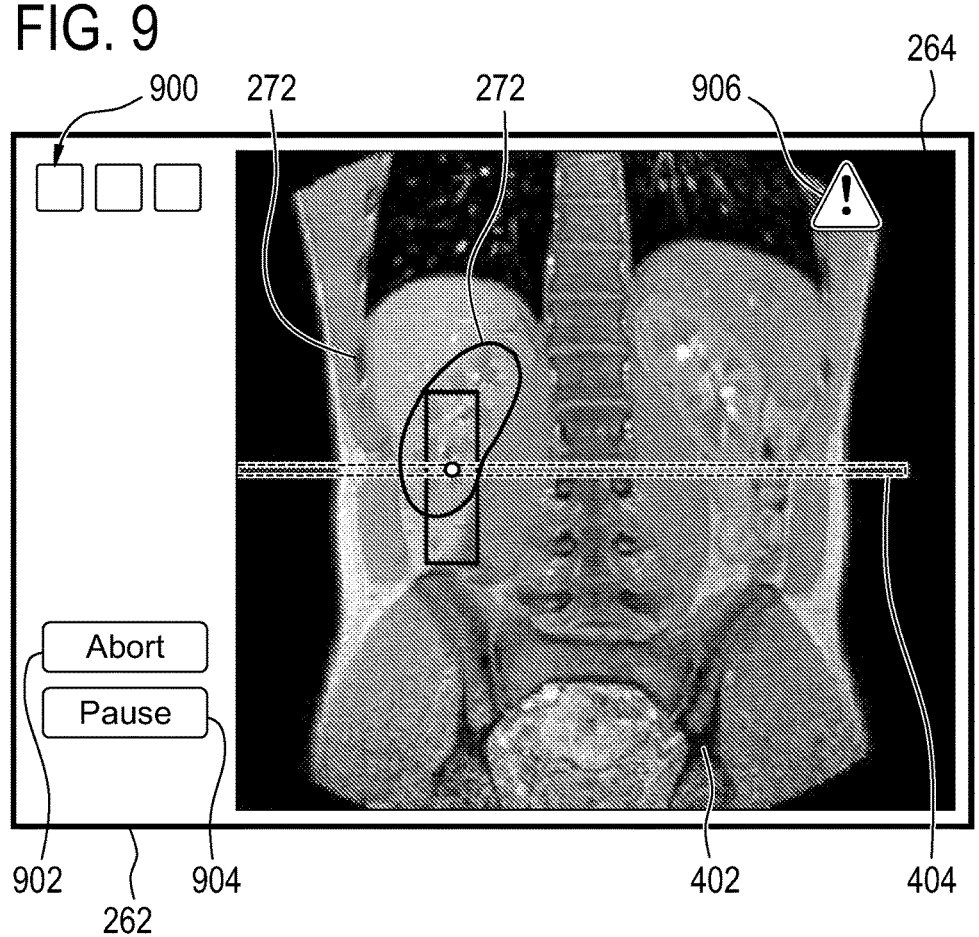
FIG. 9 illustrates another example of a graphical user interface.

FIG. 9 illustrates another example of a graphical user interface 262. In this example the medical image 264 from FIG. 4 is illustrated here. There are several anatomical references 272 shown in this Fig. The graphical user interface 262 has several template selection buttons 900 which enable an operator to automatically template which views are shown. Additionally there is an abort button 902 and a pause button 904. The abort button 902 aborts the treatment and the pause button 904 pauses the treatment. Also illustrated in FIG. 9 is a warning glyph 906 which is shown as being superimposed over the medical image 264. The warning glyph 906 may be displayed when failure descriptive of a failure to determine the second registration and/or the cumulative dose data is detected.

Figure 10:
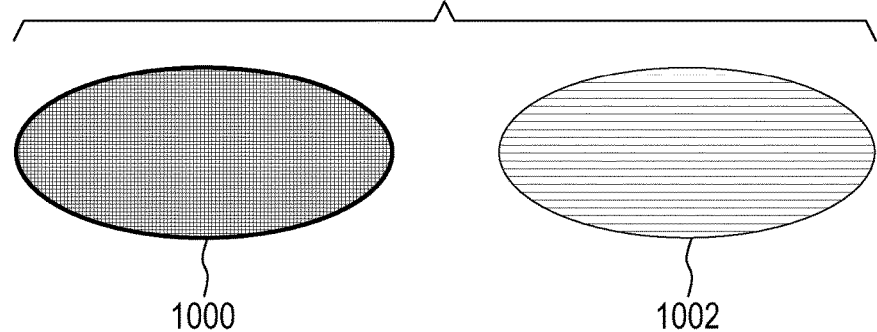
FIG. 10 illustrates how graphical objects may be displayed on a graphical user interface.

FIG. 10 illustrates how graphical objects may be displayed on the graphical user interface. If the tracking or registration of an object is successful the representation of the anatomical reference may be displayed in a first manner of fashion. In FIG. 10 the object 1000 may be an example of a representation of an anatomical reference which is showing successful tracking. The object labeled 1002 may be an example of a representation of an anatomical reference that is not being tracked. For instance the border may be dashed and the interior of the object may be a different color, a lighter color or may be more transparent.

Figure 11:
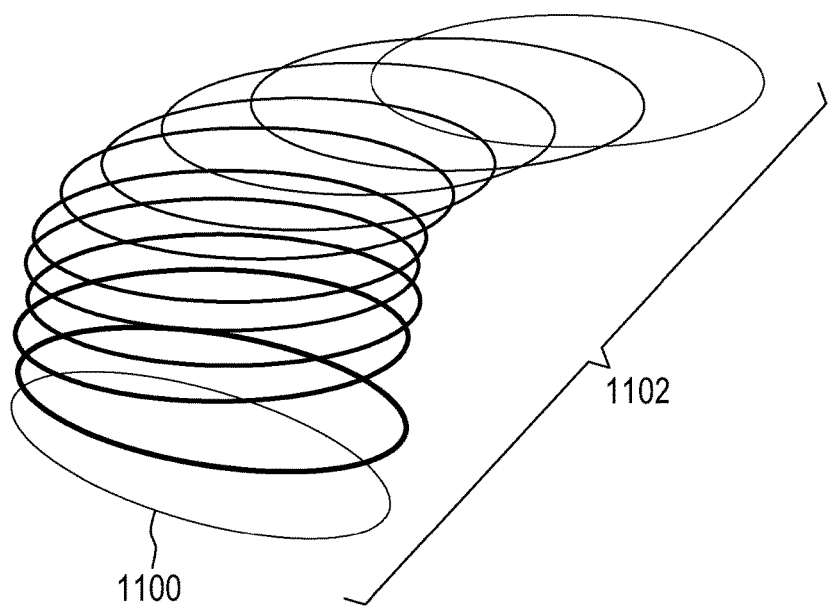
FIG. 11 illustrates as method of showing periodic motion of an object within a graphical user interface.

FIG. 11 illustrates as method of how an object may illustrate periodic motion within a graphical user interface. For instance the object 1100 could be shown multiple times 1102 each one illustrates a different position of the object 1100 at different points in phase with respect to the periodic motion of the subject. This may be useful because it will show how a portion of the subject, for instance a critical organ, may change over time and changes position relative to the treatment zone.

FIG. 12 illustrates a further method of displaying an anatomical reference to illustrate its movement over time. The outline 1200 represents an anatomical reference at time 0 with a relative phase of 0 with respect to subject periodic motion. During each particular cycle of the subject's movement the anatomical object 1200 may not return to exactly the same position. For example the position of the anatomical object may be in a different position 1202 at time 1 at the phase 0 again. This may present some difficulty to an operator trying to estimate how the anatomical reference 1200, 1202 will move over different cycles. The solution to this is to superimpose the position of the anatomical reference over several cycles. The outline 1204 is a composite of the positions of 1200 and 1202. This may give the operator a better idea of how the anatomical reference will move and allow the operator to reduce his or her cognitive burden in operating the graphical user interface.

Embodiments of the invention may relate to methods where real-time images are combined and overlaid with therapy data, such as LINAC dose estimate, and structure tracking data. It addressed the automated, templated display slice positioning, frame of reference for displaying moving objects, and visualization of tracking errors and tracking quality.

The motion correction is often indirectly measured and/or from a signal source with bad signal quality. Therefore it is important that there is human supervision for the duration of the therapy event: abnormalities in the incoming signals can be visualized and used to abort or pause the treatment.

Embodiments of the invention may relate to the ways image sets are displayed to the user during the therapy. The image set can be an a-priori acquired image set of good diagnostic quality and visualize the accrued therapeutic effect as colored overlays. For an MR-LINAC, the effect can be the estimated dose accumulated so far, and for the HIFU, the temperature or thermal dose.

In one embodiment, the diagnostic image set and the therapeutic effect is augmented by displaying the tracked organs and tissues pertinent for the therapy. These objects can be displayed as moving intersection lines, semi-opaque filled intersection areas with possible line highlighting, or as shaded, segmented 3D objects with possible intersection line highlighting. 3D objects can also be stenciled to display above/below-display-plane portions with different shades or colors (out-of-plane motion).

In another embodiment, the diagnostic image set is a-priori acquired 4D image set. The user-selected target, for example, the tumor to be treated, is located based on the incoming realtime position correction data. The position value can be the center-of-mass or similar well-defined position related to the target. The position is selected as the frame of reference for displaying the image data. It is also used to select slices from a corresponding 3D set from the 4D superset to the display. Note that the 3D set can also be a collection of 2D slices of varying orientation and even just a simple 2D slice. For the user, this means that the user-selected target seems to be fixed at display plane and morphology (organs and tissue) moves around it.

In another embodiment, tracked objects and the therapeutic effect overlay are displayed on the fixed-target display.

In another embodiment, the user can alter the display plane position and orientation. The morphological image data is interpolated to display multi-planar-reconstructed slices at the wanted position, with the optional objects and overlays modified accordingly.

In another embodiment, the a-priori acquired image set is replaced by scanning new 2D or 3D image data at the display plane position and orientation requested by the user. Scanning can be interleaved with motion correction data acquisition. In another embodiment, the user is offered interactive tools for selecting templated display plane positions: for example, for MR LINAC, a beam view at 5 fixed angles, centered on the mass-center of the tumor, can be automatically brought to display:

In another embodiment, the template can calculate with MPR or measure with newly acquired image data a plane from the target to the nearby critical structure, so that the shortest distance between target volume and the estimated worst effect on the critical structure is visualized regardless of the respective positions of the items. Tracked objects and the therapeutic effect overlays can optionally be displayed on the defined plane. The plane orientation can either be defined to contain the maximum about of the deleterious effect to the patient, or the plane can be oriented with radiological or neurological conventions, or aligned according to the therapy device conventions, such as along a beam view in an MR-LINAC.

In another embodiment, the template can display a plane between two user selected arbitrary objects, so that the shortest distance between worst effects on the structures is visualized regardless of the respective positions of the items.

In another embodiment, the user is notified about the failures in motion correction or therapy effect determination problems—when the automated organ/tissue tracking fails to locate or determine with sufficient accuracy the location and/or shape of the tracked object; or when the algorithm calculating the effect is unable to produce a result. The notification can be warning glyphs or icons on the image area.

In another embodiment, the user is notified about the failures in motion correction with tracked object graphics or therapeutic effect overlays: The object can be shown as frozen, with different line style (e.g., dotted line) and/or colors (such as dimmed or more transparent).

In another embodiment, the user is notified about the uncertainty in motion with tracked object graphics: The object can be shown with tracking history, optionally time-filtered, where the object is shown as smeared by cumulative overlapping of tracking data:

In another embodiment, the cumulative overlapping tries to match the phase in periodic motion to only overlap equiphase history of the object.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS

200 medical instrument
202 medical imaging system
204 imaging zone
206 treatment system
208 treatment zone 210 subject
212 subject support
214 computer system
216 hardware interface
218 processor
220 user interface
222 computer storage
224 computer memory
230 treatment plan
232 selection of reference location
234 selection of anatomical references
236 medical image data
238 medical image
240 cumulative dosage data
242 first registration
244 second registration
250 control module
252 image reconstruction module
254 image registration module
256 dosage calculation module
258 graphical user interface module
260 display
262 graphical user interface
264 medical image
268 reference location
270 cumulate dosage rendering
272 anatomical reference
274 halt button
300 medical apparatus
302 magnetic resonance imaging system
304 magnet
306 bore of magnet
308 imaging zone
310 magnetic field gradient coil
312 magnetic field gradient coil power supply
314 radio frequency coil
316 radio frequency transceiver
222 high intensity focused ultrasound system
324 fluid filled chamber
326 ultrasound transducer
328 mechanism
330 mechanical actuator/power supply
332 path of ultrasound
334 ultrasound window
336 gel pad
338 sonication point
400 display plane
500 display plane modification tool
502 current imaging planes
504 target
506 modified imaging plane
508 center pivot
510 pivot handle
600 templated display planes
700 viewing planes
800 viewing plane
802 center of plane
804 organ at risk
806 critical region of organ
808 distance between treatment zone and organ
900 template selection buttons
902 abort button
904 pause button
906 warning glyph
1000 successful tracking
1002 failed tracking
1100 location
1102 location over periodic motion
1200 time 0, phase 0
1202 time 1, phase 0
1204 combination of objects 1200 and 1202

The invention claimed is:

1. A medical instrument comprising:
a medical imaging system for acquiring medical image data from an imaging zone;
a treatment system for depositing energy into a treatment zone, wherein the treatment zone is within the imaging zone, wherein the treatment system is operable for depositing energy into a subject;
a display for displaying a graphical user interface to an operator, wherein the graphical user interface is operable for receiving a halt command;
a processor for controlling the medical instrument; and
a computer storage for storing machine executable instructions for execution by the processor, wherein execution of the instructions causes the processor to receive a selection of a reference location; wherein execution of the instructions further causes the processor to receive a selection of one or more anatomical references, wherein execution of the instructions further causes the processor to repeatedly:
control the treatment system depositing the energy into the subject in accordance with a treatment plan;
control the medical imaging system to acquire the medical image data;
reconstruct a medical image using the medical image data;
determine cumulative dosage data at least partially from controlling the treatment system depositing the energy into the subject, wherein the cumulative dosage data are registered to the medical image;
determine a first registration which registers the reference location to the medical image;
determine a second registration which registers the one or more anatomical references to the medical image;
render the medical image in the graphical user interface using the first registration to place the reference location in a predetermined position in the graphical user interface, such that the first registration enables the reference location to be displayed on a same position in the graphical user interface if the subject moves;
render a representation of the one or more anatomical references in the graphical user interface using the second registration;
render the cumulative dosage data in the graphical user interface, wherein the cumulative dosage data is superimposed on the medical image; and
control the treatment system to halt the depositing the energy into the subject if the halt command is received from the graphical user interface.

2. The medical instrument of claim 1, wherein execution of the instructions further causes the processor to receive display plane position data and orientation data from the user interface, wherein execution of the instructions further causes the processor to interpolate the medical image data to display multi-planar-reconstructed slices in the graphical user interface using the display position and orientation data.

3. The medical instrument of claim 1, wherein execution of the instructions further causes the processor to display a template display tool on the graphical user interface, wherein the template display tool is operable for selecting at least one template display plane position, wherein execution of the instructions further causes the processor to render the medical image in accordance with the at least one template display plane position.

4. The medical instrument of claim 3, wherein the template display plane position is operable for displaying a distance between the reference location and at least one of the one or more anatomical references.

5. The medical instrument of claim 4, wherein execution of the instructions causes the processor to determine a display plane containing the reference location and the at least one of the one or more anatomical references, and wherein the medical image is at least partially rendered along the display plane.

6. The medical instrument of claim 1, wherein execution of the instructions causes the processor to render the one or more anatomical references such that the position of the one or more anatomical references is displayed for multiple time periods.

7. The medical instrument of claim 1, wherein the computer storage further contains a four-dimensional image set descriptive of the subject, wherein the one or more anatomical references and the reference location are registered to the four-dimensional image set, wherein execution of the instructions further causes the processor to:
   determine position data using the medical image data, wherein the position data is descriptive of cyclical motion of the subject;
   select a three-dimensional subset of the four-dimensional image set using the position data; and
   render the three-dimensional subset and the one or more anatomical references as a single image in the graphical user interface, wherein the reference location is located at a second predetermined location in the graphical user interface.

8. The medical instrument of claim 7, wherein execution of the instructions further causes the processor to repeatedly replace at least a portion of the four-dimensional image set with the medical image.

9. The medical instrument of claim 7, execution of the instructions causes the processor to render the one or more anatomical references such that the position of the one or more anatomical references is displayed for at least an entire period of the cyclical motion of the subject.

10. The medical instrument of claim 7, wherein execution of the instructions further causes the processor to:
   detect a failure descriptive of a failure to determine the second registration, or the cumulative dosage data, or both; and
   render a failure notification in the graphical user interface if the failure is detected.

11. The medical instrument of claim 7, wherein execution of the instructions further causes the processor to:
   detect a tracking failure descriptive of a failure to register the cumulative dosage data and/or the one or more anatomical references to the medical image; and
   render a modified cumulative dosage data and/or representation in the graphical user interface if the tracking failure is detected.

12. The medical instrument of claim 1, wherein the treatment system is any one of the following: high intensity focused ultrasound, radio-frequency heating system, a microwave ablation system, a hyperthermia therapy system, a laser ablation system, an infrared ablation system, a tissue heating system, a radiation therapy system, a gamma knife, a charged particle treatment system, and a radiotherapy treatment system.

13. The medical instrument of claim 1, wherein the medical imaging system is any one of the following: a computer tomography system, a magnetic resonance imaging system, and a diagnostic ultrasound imaging system.

14. The medical instrument of claim 1, wherein the medical imaging system is a magnetic resonance imaging system, wherein the treatment system is a high intensity focused ultrasound system, wherein the magnetic resonance imaging system is further operable for acquiring thermal magnetic resonance data, wherein execution of the instructions further causes the processor to:
   control the magnetic resonance imaging system to acquire the thermal magnetic resonance data; and
   determine a thermal dose map from the thermal magnetic resonance data, wherein the cumulative dosage data is constructed at least partially from the thermal dose map.

15. The medical instrument of claim 1, wherein execution of the instructions further causes the processor to:
   register treatment status data to the medical image; and
   render the treatment status data in the graphical user interface, wherein the treatment status data is superimposed on the medical image, wherein the treatment status data comprises any one of the following: predictor model of treatment zone motion, position of multi-leaf collimator leaves from beam's eye view, isodose curves from the treatment plan, contour of target, critical anatomical structures, and combinations thereof.

16. A non-transitory computer-readable medium storing machine executable instructions for execution by a processor controlling a medical instrument, wherein the medical instrument comprises a medical imaging system for acquiring medical image data from an imaging zone, wherein the medical instrument further comprises a treatment system for depositing energy into a treatment zone, wherein the treatment zone is within the imaging zone, wherein the treatment system is operable for depositing energy into a subject, wherein the medical instrument further comprises a display for displaying a graphical user interface to an operator, wherein the graphical user interface is operable for receiving a halt command, wherein execution of the instructions causes the processor to receive a selection of a reference location, wherein execution of the instructions further causes the processor to receive a selection of one or more anatomical references, wherein execution of the instructions further causes the processor to repeatedly:
   control the treatment system depositing the energy into the subject in accordance with a treatment plan;
   control the medical imaging system to acquire the medical image data;
   reconstruct a medical image using the medical image data;
   determine cumulative dosage data at least partially from controlling the treatment system depositing the energy into the subject, wherein the cumulative dosage data is registered to the medical image;
   determine a first registration which registers the reference location to the medical image;
   determine a second registration which registers the one or more anatomical references to the medical image;
   render the medical image in the graphical user interface using the first registration to place the reference location in a predetermined position in the graphical user interface, the first registration enabling the reference location to be displayed on the same predetermined position if the subject moves;

render a representation of the one or more anatomical references in the graphical user interface using the second registration;

render the cumulative dosage data in the graphical user interface, wherein the cumulative dosage data is superimposed on the medical image; and control the treatment system to halt the depositing the energy into the subject if the halt command is received from the graphical user interface.

17. The non-transitory computer-readable medium of claim 16, wherein execution of the instructions further causes the processor to receive display plane position data and orientation data from the user interface, wherein execution of the instructions further causes the processor to interpolate the medical image data to display multi-planar-reconstructed slices in the graphical user interface using the display position and orientation data.

18. The non-transitory computer-readable medium of claim 16, wherein execution of the instructions further causes the processor to display a template display tool on the graphical user interface, wherein the template display tool is operable for selecting at least one template display plane position, wherein execution of the instructions further causes the processor to render the medical image in accordance with the at least one template display plane position.

19. The non-transitory computer-readable medium of claim 16 further containing a four-dimensional image set descriptive of the subject, wherein the one or more anatomical references and the reference location are registered to the four-dimensional image set, wherein execution of the instructions further causes the processor to:

determine position data using the medical image data, wherein the position data is descriptive of cyclical motion of the subject;

select a three-dimensional subset of the four-dimensional image set using the position data; and render the three-dimensional subset and the one or more anatomical references as a single image in the graphical user interface, wherein the reference location is located at a second predetermined location in the graphical user interface.

20. The computer-readable medium of claim 19, wherein execution of the instructions further causes the processor to repeatedly replace at least a portion of the four-dimensional image set with the medical image.

* * * * *